US00PP24952P3

(12) United States Plant Patent
Hill

(10) Patent No.: US PP24,952 P3
(45) Date of Patent: Oct. 7, 2014

(54) INTERSPECIFIC CORNUS HYBRID TREE NAMED 'KV10-105V1'

(50) Latin Name: ***Cornus* hybrid**
Varietal Denomination: KV10-105v1

(75) Inventor: Dennie Hill, Huntland, TN (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 72 days.

(21) Appl. No.: 13/385,877

(22) Filed: Mar. 12, 2012

(65) Prior Publication Data

US 2012/0240299 P1 Sep. 20, 2012

Related U.S. Application Data

(60) Provisional application No. 61/465,140, filed on Mar. 15, 2011.

(51) Int. Cl.
*A01H 5/00* (2006.01)

(52) U.S. Cl.
CPC ..... *A01H 5/00* (2013.01)
USPC ..... Plt./220

(58) Field of Classification Search
USPC ..... Plt./220
See application file for complete search history.

(56) References Cited

U.S. PATENT DOCUMENTS

PP7,207 P * 3/1990 Orton, Jr. ..... Plt./220

OTHER PUBLICATIONS

Anonymous. "Variegated Stellar Hybrid Dogwood" Aug. 31, 2011 available at: http://www.afterhoursnursery.com/ahndocs/ahnvarstellar.pdf.*

* cited by examiner

*Primary Examiner* — Wendy C Haas
(74) *Attorney, Agent, or Firm* — James A. Lucas; Driggs, Hogg, Daugherty & DelZoppo, Co., LPA

(57) ABSTRACT

An interspecific hybrid of *Cornus kousa* and *Cornus florida*, comprising a bud mutation of the tree covered by U.S. Plant Pat. No. 7,207. The mutation is a vigorous dogwood tree, exhibiting variegated foliage comprising green leaves with a white margin and dispersed green and mottled hues of green and white in several shades during the growing season and brilliant fall foliage with multiple shades of brilliant red-purple margins with dispersed shades of violet blue.

7 Drawing Sheets

Botanical designation: *Cornus* hybrid.
Variety denomination: 'KV10-105V1'.

BACKGROUND OF THE INVENTION

This invention relates to dogwood trees and particularly to the selection of a mutation of an $F_1$ hybrid, after the interspecific hybridization of an unnamed plant of *Cornus kousa*×a plant of *Cornus florida* 'Sweetwater'. The mutation is a sport of a patented plant (U.S. Plant Pat. No. 7,207) sold under the registered trademark STELLAR PINK®.

The particular seedlings hereof were selected from certain progeny grown in a cultivated area in Huntland, Tenn. and, as a result, have in turn been asexually reproduced by grafting. The reproduction and actual growth and selection of the new cultivar took place in the vicinity of Huntland, Tenn., has been shown to propagate true-to-type in subsequent generations of asexual reproduction and has been found to be distinctive as to its variegated foliage.

Plants of this hybrid are vigorous and upright in habit, comparable to its hybrid progenitor, and are floriferous. The broad, rounded, overlapping bracts provide a floral display from about late March through mid April in Hardiness Zones 6-7. The resistance of the plant to diseases and insects is comparable to that of the hybrid covered by U.S. Plant Pat. No. 7,207.

The plant is capable of being grown wherever plants of *C. kousa* and *C. florida* are grown although they have not been tested in any widespread areas by me or under my direction.

This mutation has been asexually reproduced by bud grafting so as to determine that it does in fact come true in successive generations. In my estimation, it has desirable commercial attractiveness due to the variegation of the leaves both during the growing season and in the fall.

In the following detailed description which includes some comments in respect to various aspects of the plant, there is provided in addition, drawings which disclose the foliage in color and the colors are referred to The R.H.S. Colour Chart published by The Royal Horticulture Society (1995) for individual notations and comments.

Figure 1:
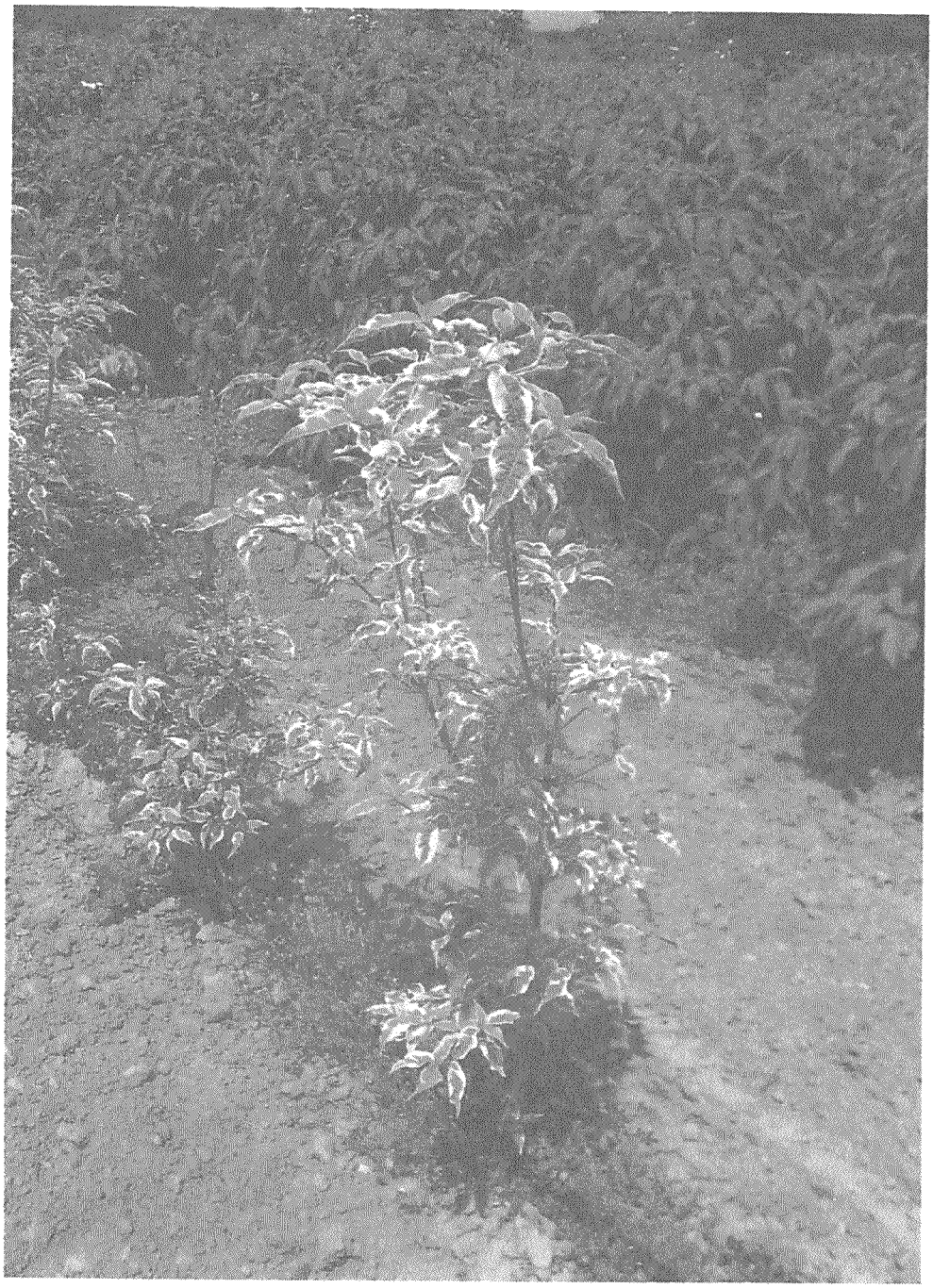
FIG. 1 discloses a tree of my new cultivar in the second full year of growth.
Figure 2:
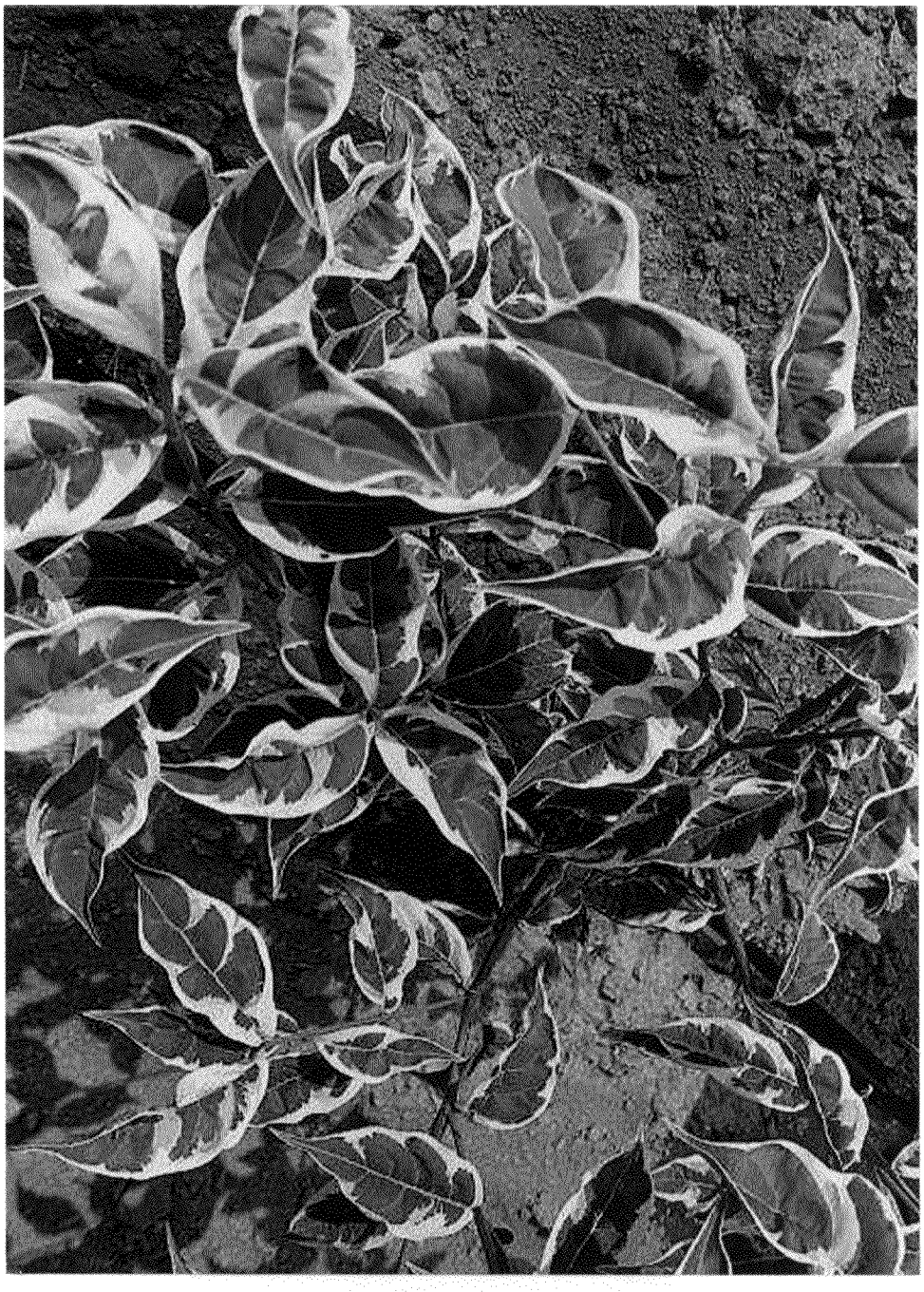
FIG. 2 (replacement) discloses the variegated leaves of this new cultivar during the growing season.
Figure 3:
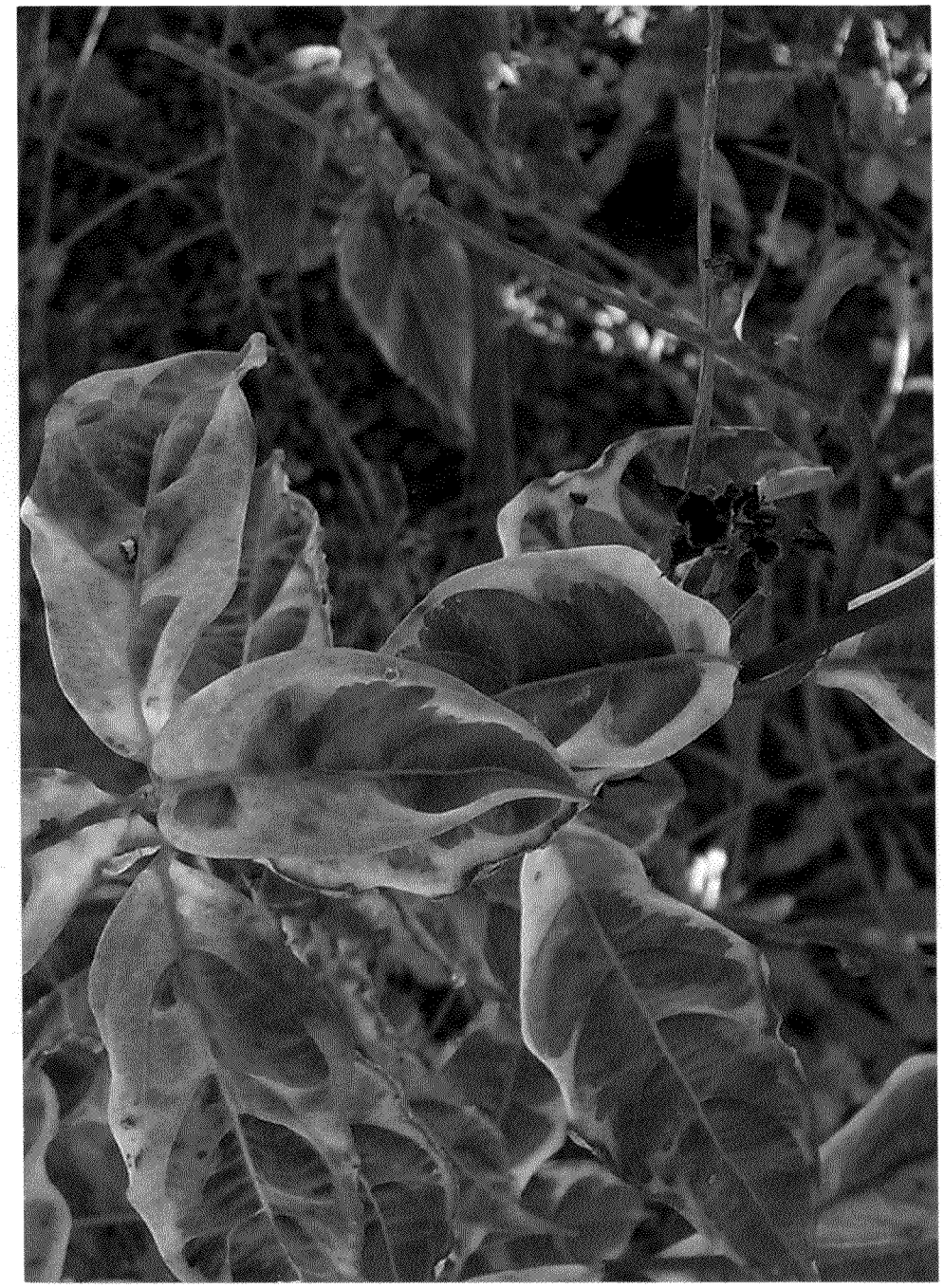
FIG. 3 (replacement) shows the variegated coloration of the leaves in late autumn.
Figure 4:
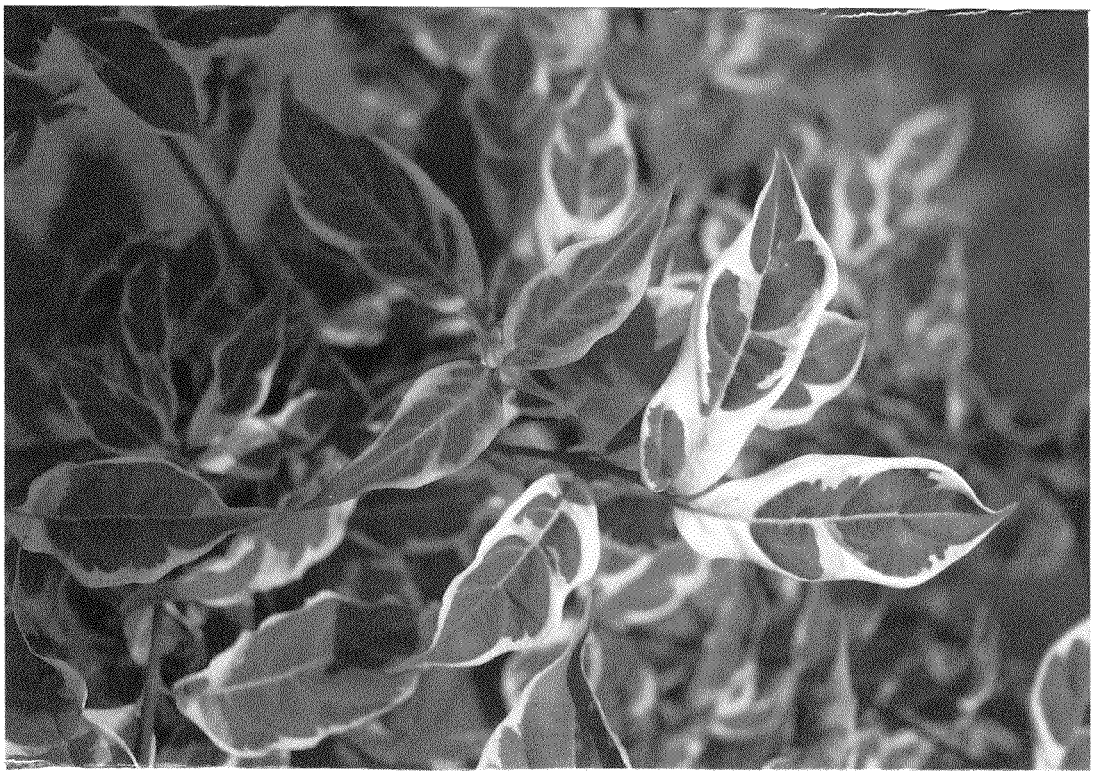
FIG. 4 shows the variegated leaves in transition from the growing season to the autumn.
Figure 5:
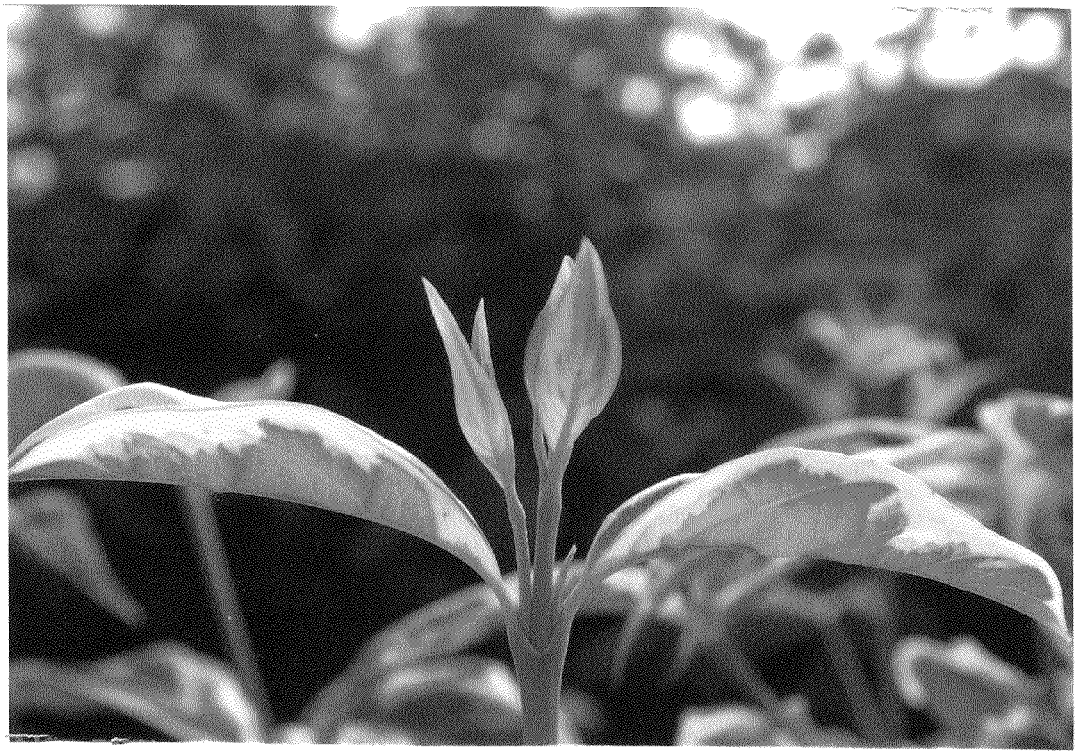
FIG. 5 shows the commencement of budding of a floral bract.
Figure 6:
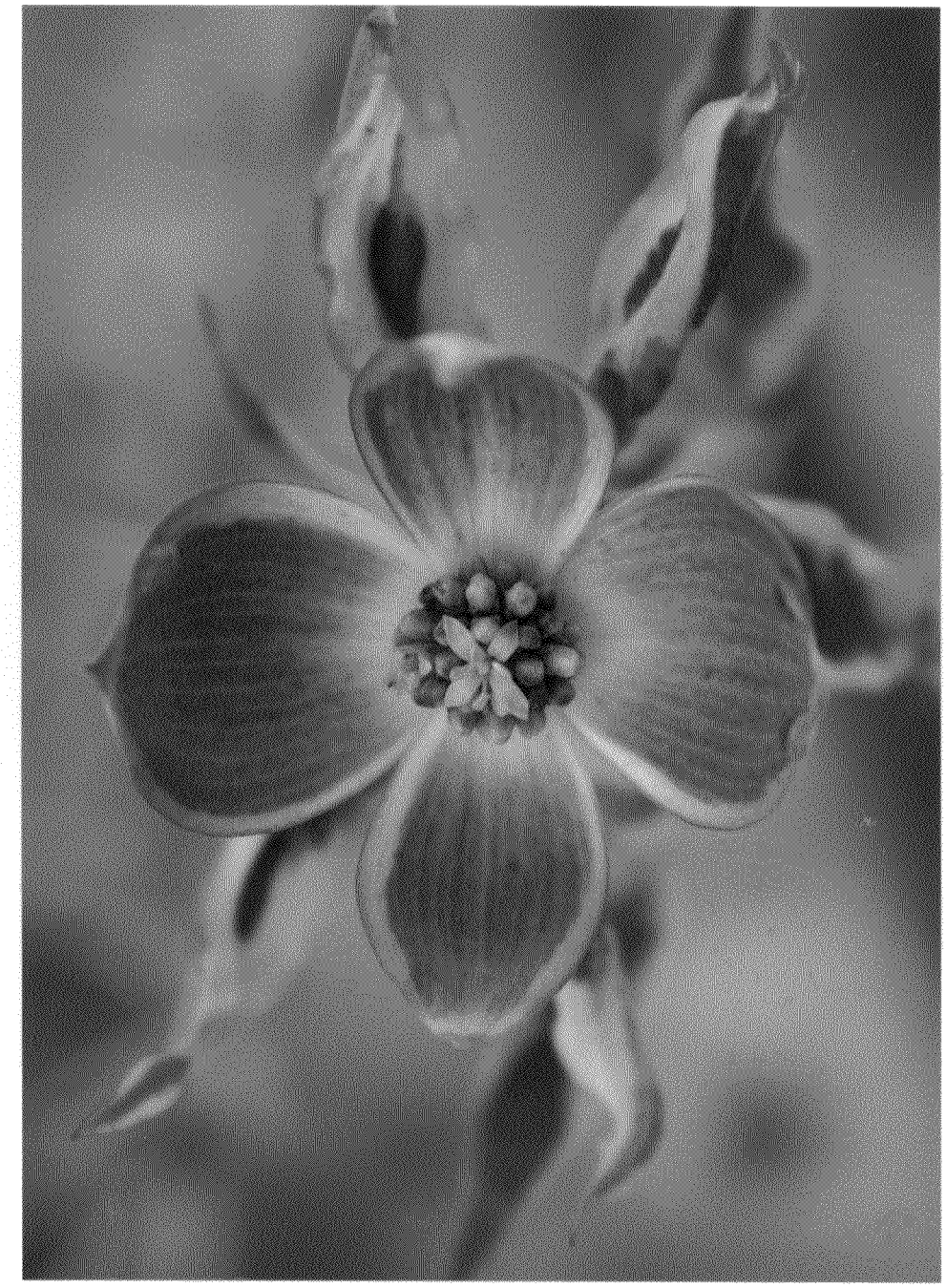
FIG. 6 (new) shows a 5 year old plant having four floral bracts with a central subtended flower head.
Figure 7:
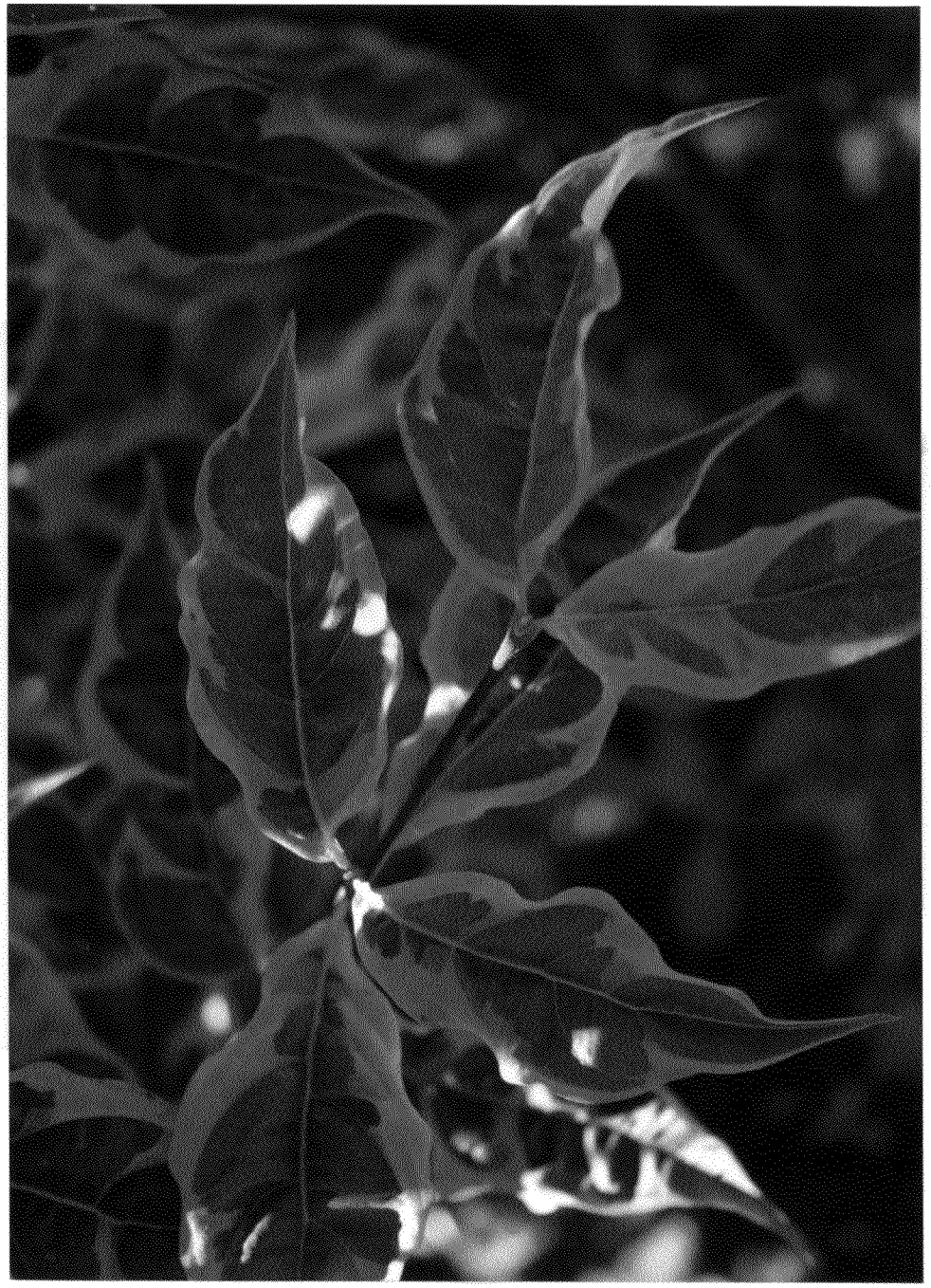
FIG. 7 (new) shows the variegated coloration of the plant leaves in early autumn.

The coloration is shown in the drawings made from digital photographs which thus reproduce the same as near as is possible to the colors of the actual plant with the notations referred thereto. Colors of foliage and other plant parts may vary from year to year depending on, among other factors, horticultural practices, light conditions, air temperature, soil fertility, etc.

BOTANICAL DESCRIPTION AND VARIETY DENOMINATION

Classification: Botanic name: $F_1$ interspecific hybrid of *C. kousa*×*C. florida.*

Commercial name: 'KV10-105v1'.

Parentage:

*Seedling.*—$F_1$ interspecific hybrid.

*Seed parent.*—Unnamed seedling of *Cornus kousa* 'Hance'.

*Pollen parent.*—*Cornus florida* L. cv. 'Sweetwater'.

PLANT

Method of asexual propagation: Grafting buds from a variegated branch mutant onto *Cornus kousa* seedling understock, holds its distinguishing leaf variegation characteristics through asexual propagation by means as grafting, budding, or rooting of softwood or semi-hardwood stem cuttings.

Tree:

*Vigorous.*—Upright and spreading, or full — dense — somewhat vase-shaped when young, but broad and full as an older plant — hardy — very productive, i.e. floriferous (but highly sterile).

Trunk:

*Medium.*—Smooth when young, and becomes somewhat shaggy with age. Colors are shades of grey brown RHS 199D.

Branches:

*Medium.*—Smooth, angles between 20° and 40° from the trunk. Color comparable to that of the trunk.

*Lenticels.*—Numerous — medium; size, color and density comparable to those of the parent $F_1$ hybrid.

Leaves: Abundant.

*Length.*—10-14 cm (average about 12.3).

*Width.*—4.8-6.6 cm (average about 5.4) at widest point. Medium size.

*Color.*—Color during growing season: white margins with varying shades between RHS 157C and RHS 155A; interior dispersed green and mottled hues of green in several shades of RHS 135D, 138C, 138D, 139C and 139D abaxial and adaxial. Color of leaves as they commence transition to fall coloration: margins, abaxial and adaxial, between white RHS 155A and light shades of red-purple 62C, and dispersed shades of red-purple 67A throughout. Color in late summer and early fall: abaxial-brilliant red-purple margins RHS 74A, and dispersed shades of grey purple RHS 187A interior and 138B-138D adaxial. Color in late fall, abaxial margins purple RHS 177 B to 177 D, and interior black RHS 202A and 202B.

*Leaf shape.*—Elliptic, with acuminate tip and cuneate base.

*Margin.*—Crenate.

*Petiole.*—6-13 mm in length (average 10.3 mm), and similar in diameter to those of U.S. Plant Pat. No. 7,207.

*Texture.*—Velvety, corrugated. The remaining observable horticultural traits of 'KV10-105v1' are similar to those of the dogwood described in expired plant patent U.S. Plant Pat. No. 7,207.

Flower buds: The true flowers are small and numerous, borne in flower heads. Typically, the true flowers are relatively inconspicuous. The actual floral display is about 12 mm. in diameter. The floral display is provided by the large floral bracts that immediately subtend the flower heads.

*Hardy.*—U.S.D.A. Plant Hardiness Zone 6a (−10 degrees F.).

*Color.*—Margins RHS 41B; Interior dispersed shades of greyed-green RHS 197A-197C.

Bracts: Floral bracts initially open with light colored marginal variegation and pinkish striations or ribs following the length of the bract. The colors of the bracts range from red purple RHS 58C on the ribs to yellow green 145B background fading to yellow green 145D at the base of bract. The back side of the bracts are yellow green 144C. When fully open, the color of the inside of the bracts is green white group RHS 157D radiating toward tips that are greyed red group 180D. Deeper pink color 58C is still observed on the ribs. Variegated margins are white 155A. Back of bracts are yellow white 155B. The bracts curve backwards at the tips and overlap slightly at the base. The bracts comprise two opposed shorter (82 mm) bracts having a width of 38 mm and two opposed longer (95 mm) but narrower (29 mm) bracts. The bracts are on petioles averaging 44 mm in length.

*Peduncle length.*—Each flower head is borne on a single peduncle. Peduncle length will vary from year to year but the relative difference between the three plants (two parents and the variegated hybrid) is quite consistent.

*Flowers.*—Date of first and full bloom: Anthesis of the tiny, relatively inconspicuous true flowers generally commences two to four days following the onset of the ornamental display of the large floral bracts, i.e. commencing in early April in zones 6-7.

REPRODUCTIVE ORGANS

Stamens:

*Number per flower.*—4. All parts of each organ are minute in size and are insignificant.

Fruit: Fully developed fruit have not been observed, as plants of this new $F_1$ interspecific hybrid are highly sterile. However, some flower heads may persist throughout the growing season and, occasionally, the fleshy portion of small, parthenocarpic (seedless) fruit will develop, albeit incompletely. However, there will be no formation of a syncarp as in *C. kousa*, as the flowers in this new hybrid are distinct and separate in the flower head, or on the receptacle.

Resistance to:

*Insects.*—Such as dogwood borer — equivalent to that of the dogwoods covered by U.S. Plant Pat. No. 7,207.

*Diseases.*—Equivalent to that of the dogwoods covered by U.S. Plant Pat. No. 7,207.

I claim:

1. A new and distinct cultivar of dogwood tree, substantially as herein shown and described, characterized particularly as to novelty by exhibiting variegated green leaves with a white margin and dispersed green and mottled hues of green and white in several shades during the growing season and brilliant fall foliage with multiple shades of brilliant red-purple margins with dispersed shades of violet blue.

* * * * *